(12) United States Patent
Schondorf et al.

(10) Patent No.: US 9,221,414 B2
(45) Date of Patent: Dec. 29, 2015

(54) IMPACT TUBING FOR PEDESTRIAN PROTECTION SENSOR FOR AUTOMOTIVE VEHICLE

(71) Applicant: Ford Global Technologies, LLC, Dearborn, MI (US)

(72) Inventors: Steven Yellin Schondorf, Dearborn, MI (US); Tim Scott, Benfleet (GB)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 14/230,296

(22) Filed: Mar. 31, 2014

(65) Prior Publication Data

US 2015/0274118 A1    Oct. 1, 2015

(51) Int. Cl.

| | |
|---|---|
| *B60R 21/34* | (2011.01) |
| *B60R 19/48* | (2006.01) |
| *B60R 21/0136* | (2006.01) |
| *B60R 21/00* | (2006.01) |

(52) U.S. Cl.
CPC ........... *B60R 19/483* (2013.01); *B60R 21/0136* (2013.01); *B60R 21/34* (2013.01); *B60R 2021/0004* (2013.01); *B60R 2021/0053* (2013.01)

(58) Field of Classification Search
CPC .. B60R 21/34; B60R 21/0136; B60R 19/483; B60R 19/20
USPC .......................... 340/436; 180/274; 73/12.04; 296/187.04
See application file for complete search history.

(56) References Cited

U.S. PATENT DOCUMENTS

| | | | |
|---|---|---|---|
| 6,561,301 | B1 | 5/2003 | Hattori et al. |
| 6,832,145 | B2 | 12/2004 | Takafuji et al. |
| 7,036,621 | B2 | 5/2006 | Takafuji et al. |
| 7,148,792 | B2 | 12/2006 | Takafuji et al. |
| 7,236,866 | B2 | 6/2007 | Takafuji et al. |
| 7,429,916 | B2 | 9/2008 | Kiribayashi |
| 7,456,382 | B2 | 11/2008 | Inamoto et al. |
| 7,493,983 | B2 | 2/2009 | Kiribayashi |
| 7,737,833 | B2 | 6/2010 | Takafuji |
| 7,916,007 | B2 | 3/2011 | Takafuji |
| 2005/0200139 | A1* | 9/2005 | Suzuki .......................... 293/117 |
| 2007/0115104 | A1* | 5/2007 | Suzuki et al. ................. 340/436 |
| 2010/0038922 | A1* | 2/2010 | Takahashi et al. ............ 293/117 |

(Continued)

FOREIGN PATENT DOCUMENTS

| | | | |
|---|---|---|---|
| DE | 10 2013 201 592 A1 | * | 8/2014 |
| EP | 1281582 | * | 2/2003 |

(Continued)

*Primary Examiner* — Ruth Ilan
(74) *Attorney, Agent, or Firm* — LeClairRyan

(57) ABSTRACT

A sensing and injury mitigation system for a vehicle to identify an object in an impact event is disclosed. The system includes an impact sensing unit comprising an impact sensor and a pressure sensing unit. The impact sensor has fluid-filled first and second tube portions. The pressure sensing unit has a housing and first and second pressure sensors located within the housing. The first tube portion of the impact sensor is attached to the first pressure sensor and the second tube portion of the impact sensor is attached to the second pressure sensor. The pressure sensing unit senses changes in fluid pressure within the tubes. In one embodiment, the tube portions of the impact sensor define a loop. In another embodiment, at least a portion of the first tube portion and at least a portion of the second tube portion share a common axis.

18 Claims, 6 Drawing Sheets

(56) References Cited

U.S. PATENT DOCUMENTS

2013/0079995 A1* 3/2013 Kula et al. .................. 701/45
2014/0052341 A1* 2/2014 Leach et al. ................ 701/45
2014/0207330 A1* 7/2014 Meir et al. ................ 701/33.9

FOREIGN PATENT DOCUMENTS

| WO | WO 2011/125147 A1 | * | 10/2011 |
| WO | WO 2012/113362 A1 | * | 8/2012 |
| WO | WO 2013/0136682 | * | 1/2013 |

* cited by examiner

IMPACT TUBING FOR PEDESTRIAN PROTECTION SENSOR FOR AUTOMOTIVE VEHICLE

TECHNICAL FIELD

The disclosed inventive concept relates generally to pedestrian protection sensors for automotive vehicles. More particularly, the disclosed inventive concept relates to a pedestrian protection sensor for a vehicle having impact tubing attached to a sensor unit.

BACKGROUND OF THE INVENTION

Pedestrian-vehicle impact events are unfortunate but known occurrences as are impact events between vehicles and non-pedestrian objects. Vehicle object impact mitigation systems are known that can identify the location and size of an object impacted by the vehicle. Where such systems are associated with the front of the vehicle it is the width and location of the impact object that helps the vehicle's impact mitigation system to determine which, if any, active restraints should be deployed. Such systems may cause the vehicle to react differently depending on whether the impact object is a pedestrian or whether it is a non-pedestrian object.

Under the former circumstance, the vehicle impact mitigation system identifies a pedestrian and actively responds to the impact event. Active responses may be both external and internal. External responses might include, but not be limited to, bumper-mounted and hood-mounted airbags and hood-lifting systems. Internal responses might include, but not be limited to, the activation of steering wheel, dashboard, and seat belt airbags or side curtains.

On the other hand, if the vehicle impact mitigation system determines that the objected impact is not a pedestrian then no external response is needed although one or more of the above-mentioned internal responses may still be mandated.

In practice, the detection of a pedestrian impact requires full sensor coverage of the front end of the vehicle to minimize the potential injury to the pedestrian, and allow other non-pedestrian objects to impact the vehicle with no system detection/reaction. One known method of accomplishing this is through the use of two pressure sensors at opposite ends of the vehicle front end connected by a sealed tube. However, this architecture is not the most cost effective because it requires a pressure sensor at each end of the tube.

Accordingly, there is a need for a simple, inexpensive device for sensing the severity, location, and width of an impact. This information may be integrated with other sensor outputs by a control system to provide an intelligent crash mitigation system.

As in so many areas of vehicle technology there is always room for improvement related to the protection of pedestrians in a pedestrian-vehicle impact event.

SUMMARY OF THE INVENTION

The disclosed inventive concept overcomes the problems associated with known impact sensing arrangements. The disclosed inventive concept provides a sensing and injury mitigation system for a vehicle to identify an object in an impact event that overcomes the limitations of known systems. Particularly, the system of the disclosed inventive concept includes an impact sensing unit that includes an impact sensor and a pressure sensing unit. The impact sensor includes a first tube portion and a second tube portion. The pressure sensing unit includes a housing. Within the housing are located a first pressure sensor and second pressure sensor. One end of the first tube portion is fluidly attached to the first pressure sensor. One end of the second tube portion is fluidly attached to the second pressure sensor. The tube portions are filled with a fluid such as a gas. The pressure sensing unit senses a change in fluid pressure within one or both of the tube portions.

According to a first embodiment of the disclosed inventive concept, the first and second tube portions form a looped pressure tube. In this embodiment, one of the tube portions is provided on the front of an energy absorber and the other tube portions is provided either to the top of or to the back of the energy absorber, thus giving some assurance that in an impact event only the tube portion on the front of the energy absorber will be crushed whereby one part of the looped tube receives the pressure wave caused by the impact and the other part of the looped tube carries the pressure wave. If the distance between the crushed area and a sensor is short, the movement of the pressure wave is relatively fast. If the distance between the crushed area and a sensor is long, the movement of the pressure wave is relatively slow. By providing a sensor at each open end of the loop, a determination as to location of the impact to the front of the vehicle can readily be made.

According to a second embodiment of the disclosed inventive concept, the first tube portion and the second tube portion are separate tubes. In the first embodiment, the first and second tube portions of the looped pressure tube are straight and parallel. In the second embodiment, at least a part of the first tube portion and at least a part of the second tube portion share a common axis.

The system includes a controller to which the pressure sensing unit is attached. The system further includes a deployable protection element for protecting an individual. The deployable protection element may be external in the form of bumper-mounted and hood-mounted airbags and hood-lifting systems. In addition, the deployable protection element may be internal in the form of one or more of steering wheel, dashboard, and seat belt airbags or side curtains.

The above advantages and other advantages and features will be readily apparent from the following detailed description of the preferred embodiments when taken in connection with the accompanying drawings.

BRIEF DESCRIPTION OF THE DRAWINGS

For a more complete understanding of this invention, reference should now be made to the embodiments illustrated in greater detail in the accompanying drawings and described below by way of examples of the invention wherein:

FIG. 3 illustrates a view of the impact sensing unit according to a preferred embodiment of the disclosed inventive concept shown relative to the bumper and energy absorber of a vehicle;

DETAILED DESCRIPTION OF THE PREFERRED EMBODIMENT

Figure 1:
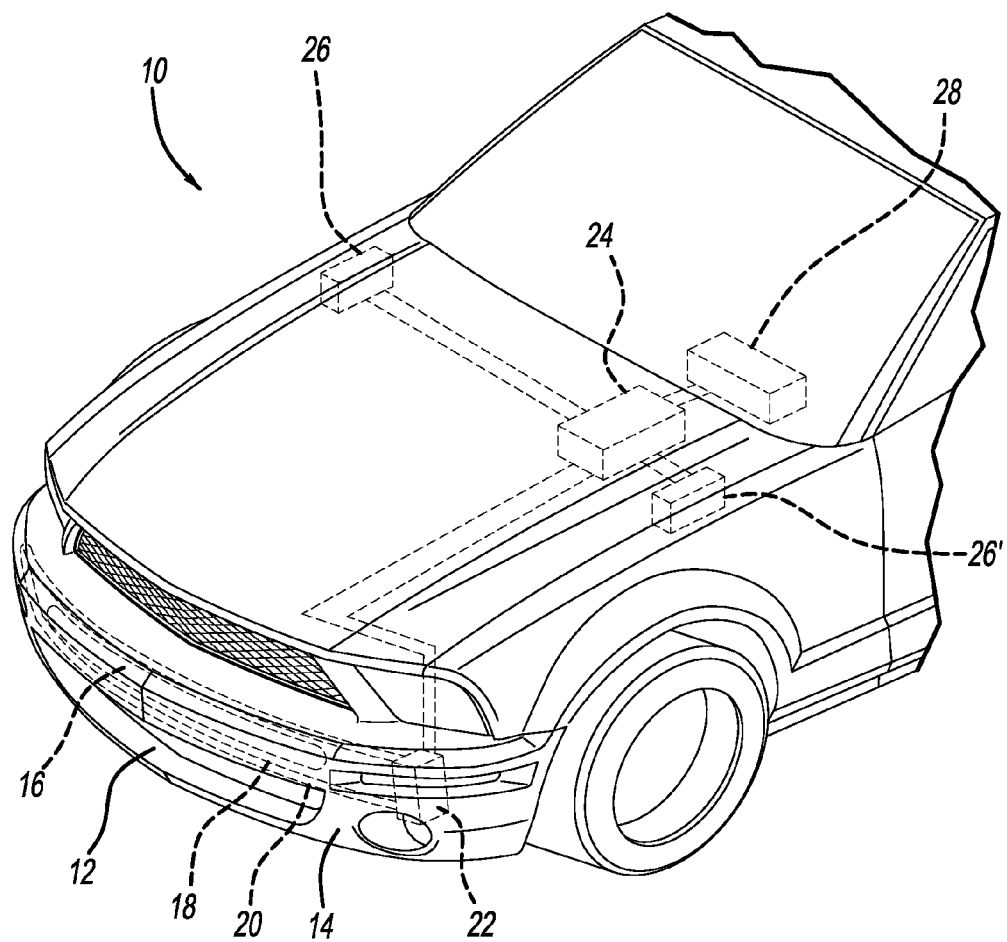
FIG. 1 is a simplified, perspective view of the forward portion of a motor vehicle including a pedestrian impact sensing system according to a preferred embodiment of the disclosed inventive concept.

In the following figures, the same reference numerals will be used to refer to the same components. In the following description, various operating parameters and components are described for different constructed embodiments. These specific parameters and components are included as examples and are not meant to be limiting.

In general, the disclosed invention provides a sensing and injury mitigation system for a vehicle that provides a more cost-effective solution compared with known technologies through the use of a single housing for both pressure sensors. In this manner a single connector to the pressure tube and a single attachment to the vehicle is provided.

The disclosed inventive concept operates to determine a pedestrian impact based on the pressure wave generated at a certain point in the looped pressure tube by an impact. By relying on one pressure sensor attached to one open end of one leg of the looped pressure tube and another pressure sensor attached to the other open end of the other leg of the looped pressure tube, a measurement of the difference in signal time and distance travelled can be made and the impact position can thus be determined. The measurement relies on only one leg of the looped pressure tube being impacted and the other leg being isolated and protected from impact by an energy absorber.

Figure 2:
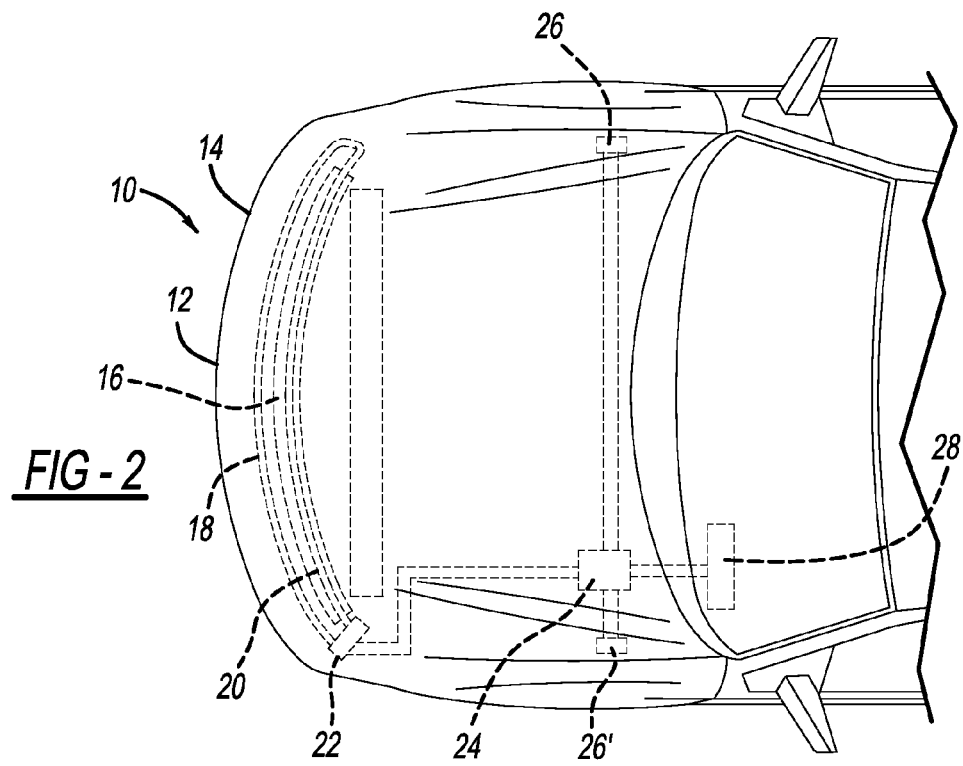
FIG. 2 is a view similar to that of FIG. 1 but illustrating a top plan view of the front end of the motor vehicle.

Referring to FIG. 1, a simplified perspective view of the forward portion of a motor vehicle, generally illustrated as 10, that includes a pedestrian impact sensing system according to a preferred embodiment of the disclosed inventive concept is illustrated. Referring to FIG. 2, a view similar to that of FIG. 1 is illustrated but shows a top plan view of the motor vehicle 10. A bumper assembly 12 is illustrated in the forward-most portion of the vehicle 10. The bumper assembly 12 is covered by a relatively thin front fascia 14 to provide both an aerodynamic contour and to improve the appearance of the underlying bumper components. The shape and overall configuration of the vehicle 10 and the bumper assembly 12 shown in FIGS. 1 and 2 are for illustrative purposes only and are not intended as being limiting.

Embedded within the vehicle 10 generally vehicle inward of the bumper assembly 12 is an energy absorber 16. The energy absorber 16 may be composed of a variety of materials but is preferably composed of impact-resistant foam or a molded polymerized material. The energy absorber 16 is provided to absorb kinetic energy when the bumper assembly 12 experiences an impact event by being crushed or flattened or otherwise deformed. The energy absorber 16 may be formed from a variety of materials, including a foamed or a thin-walled polymerized material.

The bumper assembly 12 further includes a bumper 17. Preferably but not absolutely, the bumper 17 is formed from an extruded metal, such as extruded aluminum. Alternatively, the bumper 17 may be formed from a rigid material.

Adjacent and vehicle inward of the energy absorber 16 is an impact sensing unit 18. The impact sensing unit 18 includes an impact sensor 20 and a pressure sensing unit 22. The pressure sensing unit 22 is attached to an electronic control unit 24. The electronic control unit 24 can receive a signal from the pressure sensing unit 22 indicating that an impact event has occurred as determined by the amount of pressure change in the impact sensor 20 of the impact sensing unit 18 as will be discussed in greater detail below.

The electronic control unit 24 is attached to other components of the pedestrian protection system of the vehicle 10. For example, the electronic control unit 24 may be attached to hood lift actuators 26 and 26' that raise the vehicle hood in order to create more separation between the underside of the hood and rigid components beneath the hood. This added separation allows the hood to deflect downward under the pressure of a pedestrian strike. Accordingly, signals from the electronic control unit 24 may effect triggering of the hood lift actuators 26 and 26' in order to lift the hood at an appropriate time.

The hood lift actuators 26 and 26' are examples of active pedestrian protection. Other forms of pedestrian protection that could be triggered by the electronic control unit 24 include external air bags (not shown) for protecting pedestrians.

It may be that the type of impact determined by the electronic control unit 24 in response to the pressure sensing unit 22 is of the type that is not a pedestrian impact but instead is determined to be a non-pedestrian impact. In such an instance, the electronic control unit 24 would optionally signal an internal airbag control module 28 to initiate the release of one or more interior airbags (not shown) that include but are not limited to instrument panel and steering wheel airbags and curtain airbags. It is understood that the interior airbags may be initiated in the event of a pedestrian impact as well.

Referring to FIG. 3, the pressure sensing unit 22 includes a pressure sensing unit housing 23. Within the pressure sensing unit housing 23 is a first pressure sensor 30 and a second pressure sensor 32. The impact sensor 20 includes a looped pressure tube 33 having a first leg or pressure tube portion 34 and a second leg or pressure tube portion 36. The looped pressure tube 33 and the related pressure sensors 30 and 32 contain a fluid such as a gas. The looped pressure tube 33 is preferably though not necessarily made from a flexible or semi-flexible polymerized material. Accordingly, the looped pressure tube 33 may be used in a wide range of packaging options.

The pressure sensing unit 22 of the disclosed inventive concept may optionally include a bidirectional, self-testing G-sensor 35 for safing (in order to prevent system malfunction) and a temperature sensor 37. The temperature sensor 37, if supplied, detects temperatures of the fascia 14 and the energy absorber 16 insofar as the temperatures of these components are subject to changes in ambient air temperature. The pressure sensing unit 22 may further include a piezoelectric transducer 39 for testing pressure sensitivity of the looped pressure tube 33 by generating a pressure pulse. The piezoelectric transducer 39, if supplied, checks the pressure sensitivity each time the vehicle is started.

The first pressure tube portion 34 includes an open end 38 while the second pressure tube portion 36 includes an open end 42. The first pressure tube portion 34 and the second pressure tube portion 36 are fluidly connected by a loop 44 such that the looped pressure tube 33 is continuous between the first open end 38 and the first open end 42. The open end 38 of the first pressure tube portion 34 is fluidly attached to the first pressure sensor 30 while the open end 42 of the second pressure tube portion 36 is fluidly attached to the second pressure sensor 32.

The looped pressure tube 33 of the impact sensing unit 18 is attached to the vehicle 10 by a mounting bracket 46 and the pressure sensor housing 22. Optionally the impact sensor 20 may also be attached to the vehicle 10.

Figure 4:
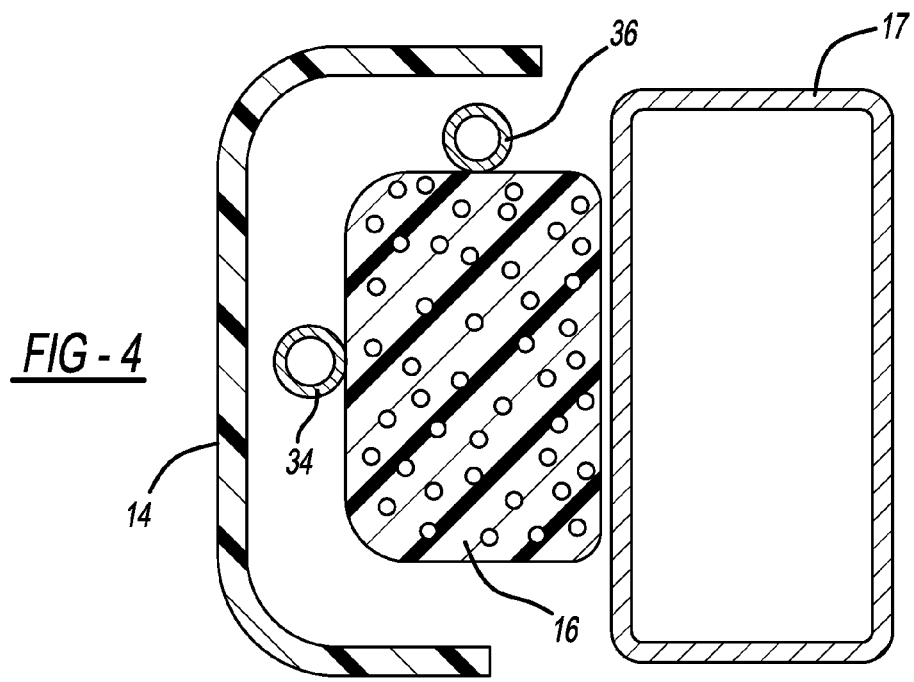
FIG. 4 illustrates a sectional view taken along line 4-4 of FIG. 3.

Referring to FIG. 4, a sectional view of FIG. 3, taken along line 4-4 of that figure, illustrates relative position of the first pressure tube portion 34 fitted adjacent to the front of the energy absorber 16 while the second pressure tube portion 36 is fitted to the top side of the energy absorber 16. It should be noted that the second pressure tube portion 36 could also be fitted to the bottom side of the energy absorber 16.

Figure 5:
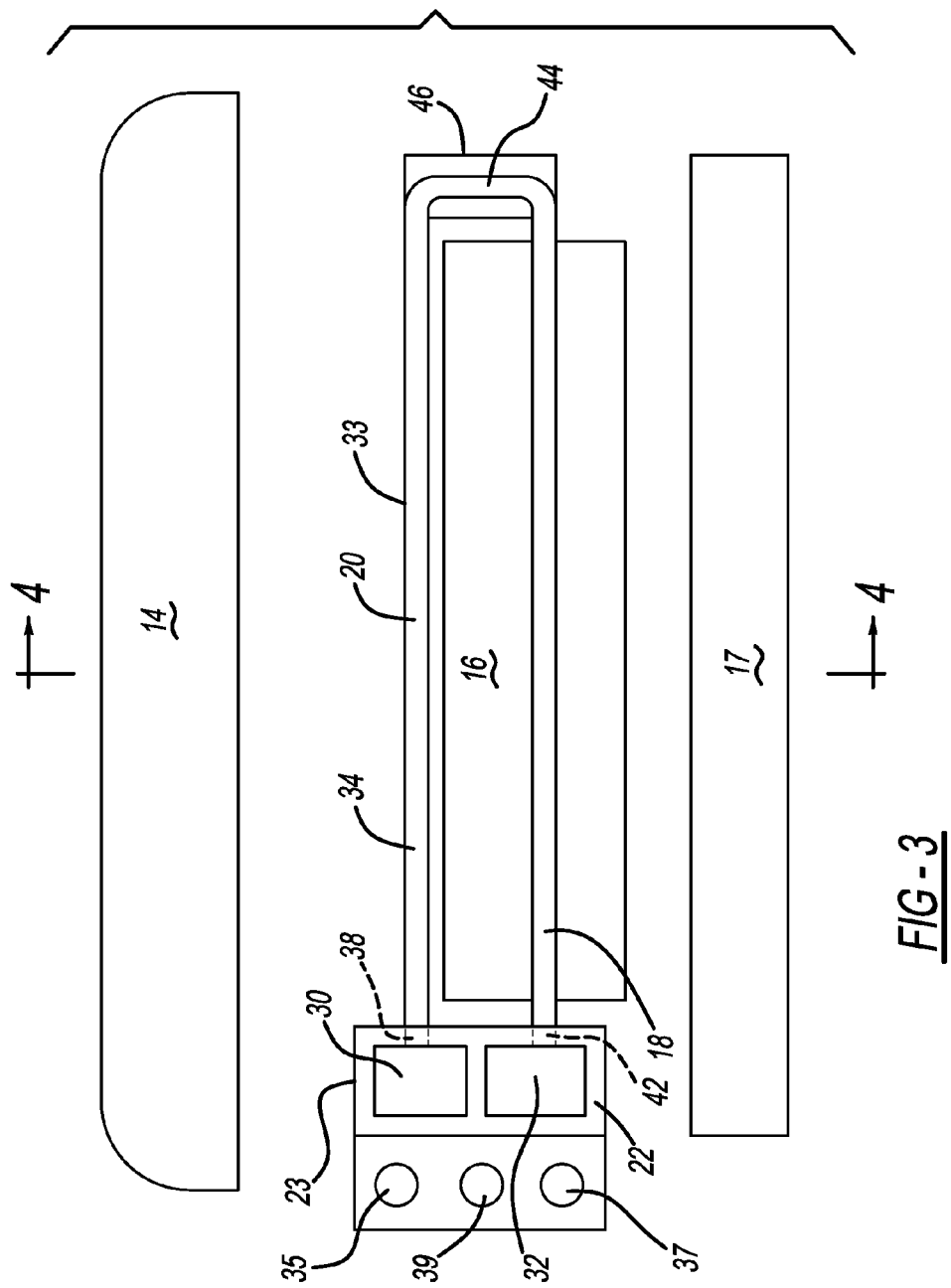
FIG. 5 is a top plan view of the impact sensing unit according to an alternative embodiment of the disclosed inventive concept positioned in the forward portion of a motor vehicle.
Figure 6:
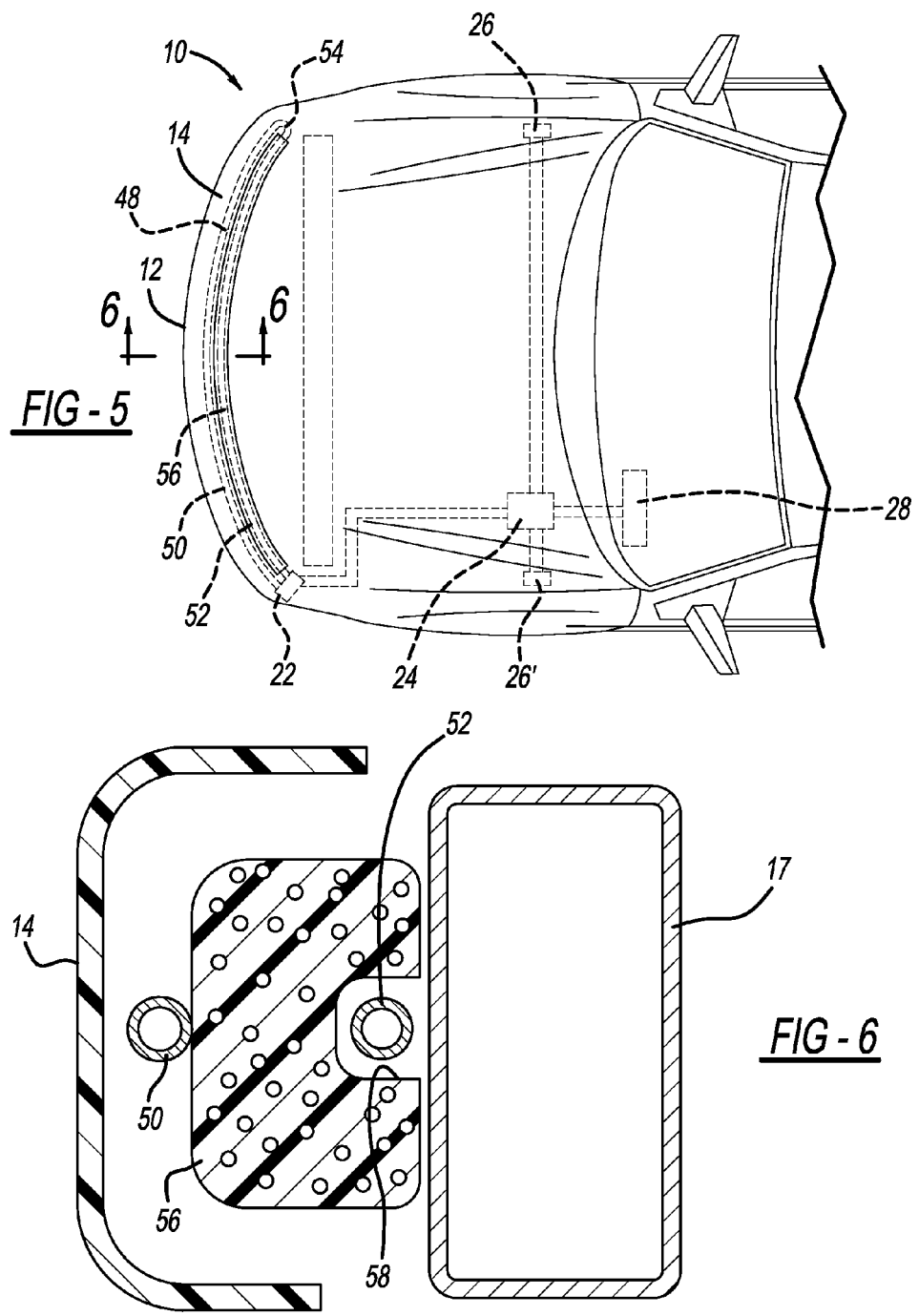
FIG. 6 illustrates a sectional view of an alternate embodiment of the arrangement of the pressure tube relative to the energy absorber and the bumper of a vehicle taken along line 6-6 of FIG. 5.

An alternative to the arrangement shown in FIGS. 1 through 4 and discussed in relation thereto is shown in FIGS. 5 and 6. FIG. 5 illustrates a top plan view of the impact sensing unit according to an alternative embodiment of the disclosed inventive concept positioned in the forward portion of a motor vehicle and FIG. 6 illustrates a sectional view of the sensing unit taken along line 6-6 of FIG. 5.

Like the embodiment of the pedestrian impact sensing system shown in FIGS. 1 through 4, the embodiment shown in FIGS. 5 and 6 includes the vehicle 10 having the bumper assembly 12 covered by the thin front fascia 14. The bumper 17 is again part of the bumper assembly 12.

A looped pressure tube 48 having a first leg or pressure tube portion 50 and a second leg or pressure tube portion 52 is provided. The first pressure tube portion 50 and the second pressure tube portion 52 are connected by a loop 54. The open ends of the looped pressure tube 48 are fluidly attached to the pressure sensing unit 22 in the same manner as described above with respect to the embodiment shown in FIGS. 1 through 4. An energy absorber 56 is provided between the fascia 14 and the bumper 17. Like the energy absorber 16 described above, the energy absorber 56 may be composed of a variety of materials but is preferably composed of impact-resistant foam or a molded polymerized material.

As shown in FIGS. 5 and 6, the first pressure tube portion 50 is fitted adjacent the front of an energy absorber 56 while the second pressure tube portion 52 is fitted into a channel 58 formed on the back side of the energy absorber 52. In this manner, the second pressure tube portion 52 is provided with protection from direct impact.

The looped pressure tubes 33 and 48 discussed above represent one approach to the pressure tube of the impact sensing unit of the disclosed inventive concept. However, this is not the only possible arrangement and an alternate pressure tube configuration is illustrated in FIGS. 7 through 10.

Figure 7:
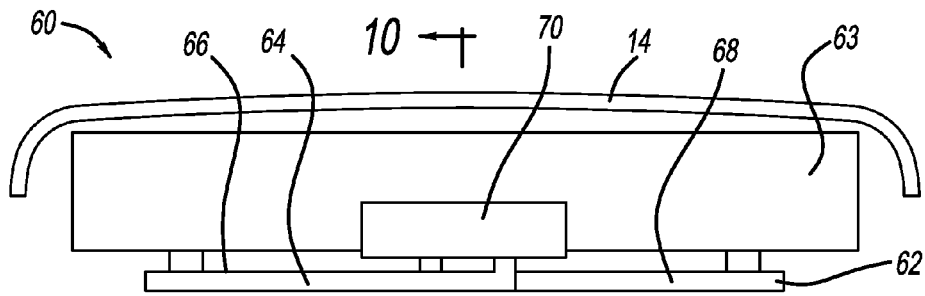
FIG. 7 illustrates a top plan view of an alternative embodiment of the pedestrian impact sensing system according to a preferred embodiment of the disclosed inventive concept.

Referring to FIG. 7, an alternative embodiment of the pedestrian impact sensing system according to the disclosed inventive concept is shown, generally illustrated as 60. The pedestrian impact sensing system 60 includes a pressure assembly 62 generally positioned adjacent to an energy absorber 63 that is itself positioned adjacent the fascia 14. The bumper 17 is positioned adjacent the pressure assembly 62.

The pressure assembly 62 comprises a pressure tube system 64 that includes a first pressure tube 66 and a second pressure tube 68. The first pressure tube 66 and the second pressure tube 68 each contain a fluid such as a gas. The tube arrangement is better illustrated in FIG. 8 which illustrates a back side view of the energy absorber 63 and the pressure tube system 64. A pressure sensor housing 70 is provided that includes a first pressure sensor 72 and a second pressure sensor 74. The open end of the first pressure tube 66 is attached to the second pressure sensor 74 and the open end of the second pressure tube 68 is attached to the first pressure sensor 72.

Figure 8:
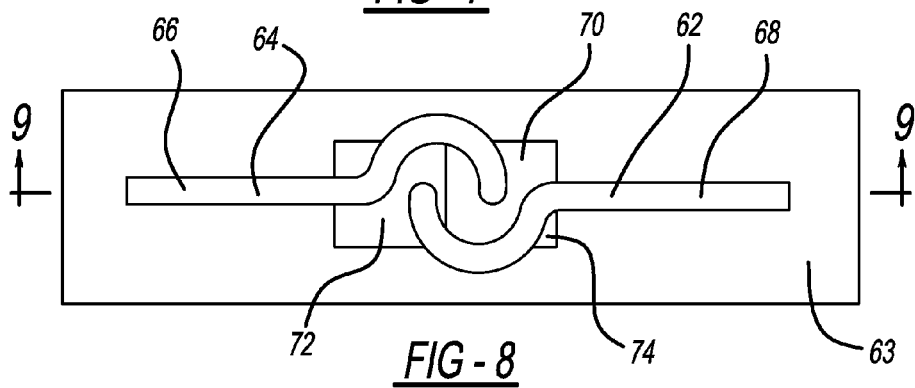
FIG. 8 illustrates a back side view of the pressure tubes positioned on the energy absorber according to the embodiment of the pedestrian impact sensing system illustrated in FIGS. 6 and 7.
Figure 9:
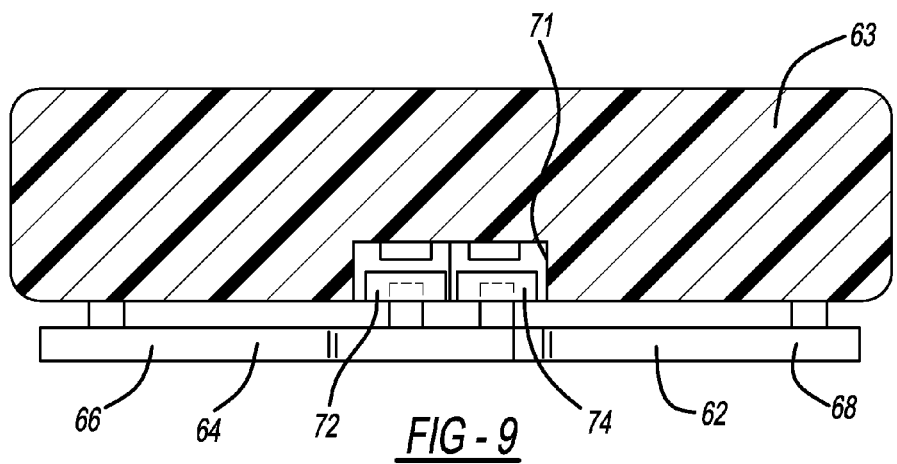
FIG. 9 illustrates a sectional view of the assembly of pressure tubes and the energy absorber taken along line 9-9 of FIG. 8.

FIG. 9 illustrates a sectional view of the energy absorber 63, the first pressure tube 66, the second pressure tube 68, the first pressure sensor 72 and the second pressure sensor 74 enclosed within the pressure sensor housing 70 (shown in FIGS. 7 and 8). The sectional view shown in FIG. 9 is taken along line 9-9 of FIG. 8. The pressure sensor housing 70 is fitted within a recessed area 71 formed in the energy absorber 63.

Figure 10:
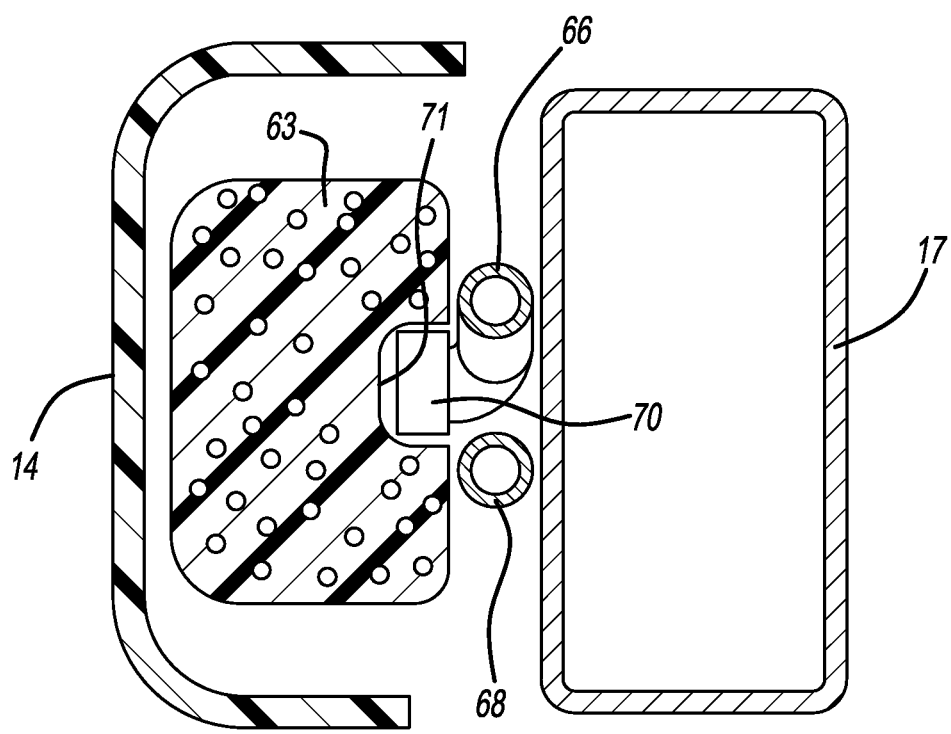
FIG. 10 illustrates a sectional view of the assembly of pressure tubes and the energy absorber taken along line 10-10 of FIG. 7.

FIG. 10, taken along line 10-10 of FIG. 7, illustrates a sectional view of the pedestrian impact sensing system 60 according to the present embodiment. As illustrated, the first pressure tube 66 and the second pressure tube 68 are positioned behind the energy absorber 63 but in front of the bumper 17.

In operation, the impact sensing unit responds with a signal to the electronic control unit 24 in an impact event. The signal is generated by the pressure sensing unit 22 (or 22') is itself a response to a change in pressure sensed in the pressure tube 33 or in either or both of the pressure tubes 66 and 68. This is made possible by a pressure transducer (not shown) associated with the pressure sensor 30 (or 72) and the second pressure sensor 32 (or 74) that generates an electrical or electronic signal representative of the sensed pressure at all times. The signals generated by the first pressure sensor 30 (or 70) and the second pressure sensor 32 (or 72) are sent to the electronic control unit 24 where they may be digitized, integrated, measured, compared or otherwise electronically and/or mathematically processed in order to detect characteristics such as the magnitude, time and location of an impact on the impact sensing unit 18 (or 18' or 70). It also may be possible to use the raw signals generated by the first pressure sensor 30 (or 72) and the second pressure sensor 32 (or 74) to actuate either a pedestrian protection element or a passenger protection element without significant processing by the electronic control unit 24.

The disclosed inventive concept provides the packaging of the two pressure sensors 30 and 32 (or 72 and 74) adjacent one another in the same pressure sensing unit housing 23 (or 70) contributes to the efficiency of the design of the overall impact sensing unit 18 (or 18') as compared with locating multiple sensors at separate, spaced apart locations. Fabrication, installation and servicing of the impact sensing unit 18 (or 18') are all improved by the unitary construction of the pressure sensing unit 22 (or 22').

Thus the disclosed invention as set forth above overcomes the challenges faced by known pedestrian protection sensing systems for vehicles by reducing both complexity and cost. However, one skilled in the art will readily recognize from such discussion, and from the accompanying drawings and claims that various changes, modifications and variations can be made therein without departing from the true spirit and fair scope of the invention as defined by the following claims.

What is claimed is:

1. A sensing and injury mitigation system for a vehicle to identify an object in an impact event, the system comprising:
an impact sensor including first and second tubes, each of said tubes including an arcuate portion and a straight portion;
a first pressure sensor to which said first tube is attached;
a second pressure sensor to which said second tube is attached, said arcuate portion of said first tube being connected to said first pressure sensor and said arcuate portion of said second tube being connected to said second pressure sensor; and a housing within which said pressure sensors are located.

2. The sensing and injury mitigation system for a vehicle of claim 1 wherein said straight portions of said first and second tubes having a common axis.

3. The sensing and injury mitigation system for a vehicle of claim 2 wherein said straight portion of said first tube extends from said arcuate portion of said first tube and said straight portion of said second tube extends from said arcuate portion of said second tube.

4. The sensing and injury mitigation system for a vehicle of claim 3 wherein a portion of said arcuate portion of said first tube overlaps a portion of said arcuate portion of said second tube.

5. The sensing and injury mitigation system for a vehicle of claim 4 wherein said tubes are filled with a fluid and said pressure sensors sense changes in fluid pressure in said first and second tubes.

6. The sensing and injury mitigation system for a vehicle of claim 1 further including a bumper and an energy absorber, said energy absorber having a front side and a back side, said first and second tubes being fitted adjacent said back side.

7. The sensing and injury mitigation system for a vehicle of claim 6 wherein said energy absorber has a pocket formed in said back side, said housing being fitted in said pocket.

8. The sensing and injury mitigation system for a vehicle of claim 6 wherein said energy absorber has a long axis, wherein said straight portion of said first tube and said straight portion of said second tube have a common axis, and wherein said common axis shared by said portions of said tubes is parallel with said long axis of said energy absorber.

9. A sensing and injury mitigation system for a vehicle to identify an object in an impact event, the system comprising:
   an impact sensor including a first tube having arcuate and straight portions and a second tube having arcuate and straight portions;
   a first pressure sensor to which said first tube is attached;
   a second pressure sensor to which said second tube is attached, said arcuate portion of said first tube being connected to said first pressure sensor and said arcuate portion of said second tube being connected to said second pressure sensor; and
   a housing within which said pressure sensors are located.

10. The sensing and injury mitigation system for a vehicle of claim 9 wherein said straight portion of said first tube and said straight portion of said second tube have a common axis.

11. The sensing and injury mitigation system for a vehicle of claim 9 wherein said straight portion of said first tube extends from said arcuate portion of said first tube and said straight portion of said second tube extends from said arcuate portion of said second tube.

12. The sensing and injury mitigation system for a vehicle of claim 9 wherein a portion of said arcuate portion of said first tube overlaps a portion of said arcuate portion of said second tube.

13. The sensing and injury mitigation system for a vehicle of claim 9 further including a bumper and an energy absorber, said energy absorber having a front side and a back side, said first and second tubes being fitted adjacent said back side.

14. The sensing and injury mitigation system for a vehicle of claim 13 wherein said energy absorber has a pocket formed in said back side, said housing being fitted in said pocket.

15. The sensing and injury mitigation system for a vehicle of claim 14 wherein said straight portion of said first tube and said straight portion of said second tube have a common axis and wherein said energy absorber has a long axis and wherein said common axis shared by said portions of said tubes is parallel with said long axis of said energy absorber.

16. The sensing and injury mitigation system for a vehicle of claim 9 wherein said tubes are filled with a fluid and said pressure sensors sense changes in fluid pressure in said first and second tubes.

17. A sensing and injury mitigation system for a vehicle to identify an object in an impact event, the system comprising:
   an impact sensor including first and second tubes, each of said tubes including an arcuate portion;
   a first pressure sensor to which said first tube is attached;
   a second pressure sensor to which said second tube is attached, said arcuate portion of said first tube being connected to said first pressure sensor and said arcuate portion of said second tube being connected to said second pressure sensor;
   an energy absorber having a pocket; and
   a housing for holding said pressure sensors, said housing being fitted substantially in said pocket.

18. The sensing and injury mitigation system for a vehicle of claim 17 wherein said first tube includes a straight portion extending from said arcuate portion of said first tube and said second tube includes a straight portion extending from said arcuate portion of said second tube, said straight portions having a common axis.

\* \* \* \* \*